US012383662B2

(12) United States Patent
Leven

(10) Patent No.: US 12,383,662 B2
(45) Date of Patent: Aug. 12, 2025

(54) HEATING SYSTEM WITH LOW LEAKAGE CURRENT

(71) Applicant: Debiotech S.A., Lausanne (CH)

(72) Inventor: Séverin Leven, Lausanne (CH)

(73) Assignee: NEXTKIDNEY SA, Lausanne (CH)

( * ) Notice: Subject to any disclaimer, the term of this patent is extended or adjusted under 35 U.S.C. 154(b) by 905 days.

(21) Appl. No.: 17/442,422

(22) PCT Filed: Apr. 1, 2020

(86) PCT No.: PCT/IB2020/053088
§ 371 (c)(1),
(2) Date: Sep. 23, 2021

(87) PCT Pub. No.: WO2020/202022
PCT Pub. Date: Oct. 8, 2020

(65) Prior Publication Data
US 2022/0184286 A1    Jun. 16, 2022

(30) Foreign Application Priority Data

Apr. 5, 2019   (EP) .................................... 19167705
Apr. 8, 2019   (EP) .................................... 19167988
Apr. 9, 2019   (EP) .................................... 19168278

(51) Int. Cl.
*A61M 1/16*       (2006.01)
*A61M 1/28*       (2006.01)
(Continued)

(52) U.S. Cl.
CPC ........ *A61M 1/1664* (2014.02); *A61M 1/1629* (2014.02); *A61M 1/166* (2014.02);
(Continued)

(58) Field of Classification Search
CPC .. A61M 1/1629; A61M 1/1664; A61M 1/166; A61M 1/28; A61M 1/3623; A61M 5/44; A61M 2205/36
See application file for complete search history.

(56) References Cited

U.S. PATENT DOCUMENTS 10,596,309 B2    3/2020  Thiebaud
10,940,256 B2    3/2021  Thiebaud
(Continued)

FOREIGN PATENT DOCUMENTS

WO    WO 2012155149 A2    11/2012
WO       2015162593 A1    10/2015
(Continued)

OTHER PUBLICATIONS

International Search Report mailed on Aug. 10, 2020, for Application No. PCT/IB2020/053088.
(Continued)

*Primary Examiner* — John Kim
(74) *Attorney, Agent, or Firm* — Nixon & Vanderhye

(57) ABSTRACT

A heating system for medical fluid that comprises a receptacle for medical fluid to be heated, a heating element powered by a power supply inducing a leakage current (to ground) ranging between 100 and 10 μA. The heating system further comprises an interface device (for example, an electrical insulation and thermal interface device) disposed between the heating element and the medical fluid contained in the receptacle, allowing the heating system to induce a leakage current in the medical fluid that is less than 10 μA at the applied part.

16 Claims, 7 Drawing Sheets

(51) Int. Cl.
*A61M 1/36* (2006.01)
*A61M 5/44* (2006.01)
(52) U.S. Cl.
CPC ............. *A61M 1/28* (2013.01); *A61M 5/44* (2013.01); *A61M 1/3623* (2022.05); *A61M 2205/36* (2013.01)

(56) References Cited

U.S. PATENT DOCUMENTS

2003/0220598 A1* 11/2003 Busby ................. A61M 1/155
          210/257.2
2017/0065758 A1   3/2017 Wallinger et al.
2020/0316283 A1  10/2020 Vecten

FOREIGN PATENT DOCUMENTS

| WO | WO 2015162593 | 10/2015 |
| WO | 2019087096 A1 | 5/2019 |
| WO | 2019087103 A1 | 5/2019 |
| WO | WO 2019087096 | 5/2019 |
| WO | WO 2019087103 | 5/2019 |

OTHER PUBLICATIONS

Written Opinion of the ISA mailed on Aug. 10, 2020, for Application No. PCT/IB2020/053088.

* cited by examiner

HEATING SYSTEM WITH LOW LEAKAGE CURRENT

CROSS REFERENCE TO RELATED APPLICATIONS

The present application is an United States national stage application of International patent application PCT/IB2020/053088 filed on Apr. 1, 2020 designating the United States, and claims foreign priority to three (3) European Patent Applications with the Serial Numbers EP 19167705.3 filed on Apr. 5, 2019, EP 19167988.5 filed on Apr. 8, 2019, and EP 19168278.0 filed on Apr. 9, 2019, the contents of all four (4) documents being herewith incorporated by reference in their entirety.

FIELD OF THE INVENTION

The present invention generally relates to a medical system adapted to heat a fluid, for example, a dialysis machine comprising a heating system. More specifically, the invention can relate to a heating system, an arrangement or a method for heating a fluid.

PRIOR ART

Some medical appliances require an extremely low patient leakage current level. This is particularly the case for applications where the applied part is directly in contact with or very close to the heart of the patient ("direct cardiac application"). The applied part in this case must meet a "cardiac floating (CF)" level, which is equivalent to a patient leakage current that is less than or equal to 10 μA during normal operation.

Depending on the power required to power the appliance, it is not economically and/or technically possible to find a commercially available power supply that itself meets the requirements of the CF leakage current level. Indeed, for example, the commercially available power supplies with high enough power (for example, >100 W) are generally classified for the "body floating (BF)" level, and not for "cardiac floating (CF)". A BF level corresponds to patient leakage currents ranging up to 100 uA during normal operation, therefore ten times higher compared to the CF level.

FIG. 1 shows an embodiment of the appliances of the prior art. In this example, the system (1) comprises a medical appliance (2) powered by an external electrical source (3) connected to ground. The applied parts are connected to ground, in this way the leakage currents are reduced by virtue of the grounding (for example, on the secondary side of the power supply or on the applied parts). However, this means that the manufacturers stipulate that the electrical power supply (to which the appliance is connected) is checked by a certified electrician before their appliance is used. Therefore, the patient is forced to always carry out these treatments at the same locations, in their home or in a dialysis centre, for example. This type of appliance drastically limits the freedom of these patients, since it is difficult to contemplate (even simply impossible) calling upon a certified electrician in a hotel bedroom, in the homes of friends, etc.

Furthermore, in general, in the case whereby the medical appliance is intended for domestic use, it is preferable to start from the principle that the leakage currents will not be reduced by grounding on the secondary side of the power supply or the applied parts, since this grounding can be defective or inexistent. Consequently, work must be carried out on the electrical insulations between the power supply and the applied part that comes into contact with the patient, which could allow a class II power supply to be selected (without grounding protection).

In some treatments, to avoid cooling the patient, some of the fluids used for the treatment may need to be heated. Thus, some medical appliances can be configured to heat these fluids. In the case of peritoneal or extracorporeal (in particular, haemodialysis) dialysis treatment, the medical appliance can heat the dialysate. Therefore, an electrical heating device can be integrated in the medical appliance. However, these heating devices can require a powerful power supply (as previously discussed) generating significant leakage currents that propagate through the fluid paths reaching the applied parts in contact with the patient. For example, extracorporeal dialysis treatment can require connecting the medical appliance to the patient via a central venous catheter. With the applied part being extremely close to the heart, said applied part absolutely must be of the CF type.

An example of a system (1) is schematically shown in FIG. 2. The system (1) comprises a medical appliance (2) powered by an external source (3) (for example, 85-260 VAC). The medical system (1) is configured to treat a patient (4). The medical system can further comprise a fluid container (5) heated by a heating device (6) and fluidly connected, or at least electrically connected (7), to the patient (4). The medical appliance (2) can be designed to meet the standards of class II appliances, without grounding protection. The appliance can comprise a power supply (8) with an AC-DC converter (9).

The heating device (6) can comprise a plate with resistive coils that convert the electrical energy into heat. Its power supply can originate from the AC-DC converter (9) connected to the mains (external electrical source (3)). The converter separates (insulation) the primary from the secondary, which is equivalent to two means of patient protection ("MOPP") from the mains voltage. However, even if a power supply is perfectly designed, a certain amount of parasitic capacitance (10) exists, which is a significant source of leakage current. A second electrical insulation can be arranged between the coils and the liquid so as to prevent the current from propagating towards the liquid. This insulation is formed by one or more sheets of solid, electrically insulating material.

However, the existence of these insulations does not provide protection against leakage currents (patient). Indeed, preliminary tests with a plurality of AC-DC converters (class II, BF) have shown that a CF level of leakage currents cannot be achieved despite the secondary insulation (electrical insulation) between the heating coils and the liquid (for example, an ionic liquid such as dialysate). Consequently, significant electrical coupling (11) exists between the heating device (for example, the resistive electrical conductors) and the fluid to be heated, which generates leakage currents in the fluid without direct contact with the heating device.

Normally, electrical coupling is only possible in the presence of an alternating voltage. Some of the ripple of the mains at the input of the AC-DC converters therefore must propagate from the primary to the secondary. Notwithstanding the fact that the converters supply a direct current stabilized voltage, the absolute voltage of the secondary side relative to ground is subject to this ripple.

Thus, as shown in FIG. 2, electrical coupling (11) (contactless, without propagation of the current), which can be inductive and/or capacitive, for example, between the coils and the fluid to be heated is possible and can induce a leakage current (12), the intensity of which depends on the coupling of all the elements of the system. The leakage currents at the frequency of the electrical network (50/60 Hz) that are always present on the side of the coils can induce alternating currents in the liquid, and therefore in the applied part, without immediate electrical contact.

The subject matter of the disclosure is particularly useful for medical appliances that require a certain power level and that are configured to be used with any external electrical source. In particular, it can involve medical appliances for treating chronic illness and that can be easily moved with the patient in order to improve their quality-of-life, to facilitate their treatments when travelling, etc.). Even though certified CF power supplies exist, these power supplies are very expensive and bulky, which is totally incompatible with a medical system adapted to be easily moved with the patient. Furthermore, these CF power supplies are generally adapted for lower powers; therefore, they will not be adapted for devices requiring powers that are greater than 50 W, preferably greater than 75 W, and more preferably greater than 100 W. Furthermore, these CF power supplies are sometimes limited to use with a 110-120 V electrical network and do not achieve the CF level with a 220-240 V electrical network (or more generally higher than 150 V).

GENERAL DESCRIPTION OF THE INVENTION

One of the aims described in this document is to overcome the aforementioned defects and, preferably, to achieve leakage currents that are less than 10 μA.

A first aspect of the disclosure relates to a heating system for medical fluid comprising a receptacle for medical fluid to be heated, an applied part fluidly connected to the medical fluid and intended to be in contact with a patient, an electrical power supply inducing a leakage current ranging between 100 and 10 μA, a heating element intended to heat the medical fluid and powered by the electrical power supply and an interface device disposed between the heating element and the fluid to be heated that is contained in the receptacle.

The heating element and/or the interface device are adapted to limit the inductive and/or capacitive coupling so that the leakage currents (to ground) of the applied parts are less than 10 μA.

According to some embodiments, the heating element comprises conductors (for example, resistive conductors), a section of which can be a round or another shape. According to some embodiments, the heating element comprises strips (for example, resistive strips), the widths of which are disposed vertically. According to other embodiments, the heating element comprises strips (for example, resistive strips), the widths of which are disposed horizontally.

According to some embodiments, the interface device comprises a composite material. The composite material can comprise at least the following elements: borosilicate, vitroceramic, aluminium oxide, aluminium nitride, silicon nitride, boron nitride, metal particles, ceramic particles, silicon filled with metal or ceramic particles.

According to some embodiments, the composite material can be characterized by:
  low relative dielectric permittivity, good thermal conductivity and low specific heat;
  relative dielectric permittivity that is less than 6 or less than 5 or less than 4 (for example, ranging between 5.5 and 3); and/or
  thermal conductivity that is greater than 5 W/mK or 6 W/mK.

According to some embodiments, the interface device comprises a heat transfer device comprising a heat transfer fluid.

According to some embodiments, the interface device comprises a capacitive or inductive magnetic shielding.

According to some embodiments, the applied part is in contact with the heart, the myocardium or a cavity contiguous to the heart of a patient.

According to some embodiments, the electrical power supply comprises an insulated AC-AC or AC-DC converter.

According to some embodiments, the electrical power supply is not connected to ground.

Another aspect of the invention relates to a dialysis treatment system comprising a heating system as disclosed in this document.

According to some embodiments, the liquid to be heated is blood or dialysate.

According to some embodiments, the applied part comprises a central venous catheter or a long peripheral venous catheter.

A second aspect of the disclosure relates to a heating system configured to heat a fluid electrically connected to a patient. The heating system can comprise an electrical power supply not connected to ground inducing a leakage current that is greater than 10 μA, a heat source powered by the electrical power supply and an insulating layer disposed between the heat source and the fluid to be heated.

Preferably, the insulating layer comprises an electrically insulating material and it can be designed so that the leakage current (to ground) of the system transferred to the fluid to be heated is less than or equal to 10 μA, whilst allowing optimal heat transfer from the heat source to the fluid to be heated.

The insulating layer and the heat source can be disposed as a blanket, where the insulating layer can be sandwiched between the heat source and the fluid to be heated. The thickness of the insulating layer can be substantially equal to or less than 10 mm, preferably substantially equal to or less than 8 mm, more preferably substantially equal to or less than 7 mm, for example, ranging between 6.5 and 4 mm (or less).

According to some embodiments, the heat source comprises resistive coils and the insulating layer can be arranged at least above the resistive coils. Preferably, the insulating layer fully covers the heat source.

Preferably, the insulating layer comprises high thermal conductivity, high electrical resistance and/or a low dielectric constant. It can have isotropic thermal conductivity.

According to some embodiments, the specific heat capacity of the insulating layer is substantially equal to or less than 1,400 $J \cdot Kg^{-1} \cdot K^{-1}$, preferably substantially equal to or less than 1,200 $J \cdot Kg^{-1} \cdot K^{-1}$, more preferably substantially equal to or less than 1,100 $J \cdot Kg^{-1} \cdot K^{-1}$.

According to some embodiments, the thermal conductivity of the insulating layer is substantially equal to or greater than 4 $W \cdot m^{-1} K^{-1}$, preferably equal to or greater than 5 $W \cdot m^{-1} K^{-1}$, more preferably equal to or greater than 5 $W \cdot m^{-1} K^{-1}$, for example, ranging between 5 and 6 $W \cdot m^{-1} K^{-1}$.

According to some embodiments, the dielectric constant of the insulating layer is substantially equal to or less than 5, preferably equal to or less than 4, more preferably equal to or less than 3, for example, ranging between 5.5 and 3 (or less).

The insulating layer can comprise a silicon elastomer, boron nitride, a ceramic filled silicon elastomer (that can comprise boron nitride), borosilicate, vitroceramic, aluminium oxide, aluminium nitride, silicon nitride, boron nitride, metal particles, ceramic particles, silicon filled with metal or ceramic particles.

According to some embodiments, the system further comprises a first heat transfer layer comprising a heat-conducting material configured to transfer the heat from the heat source to the fluid to be heated. The insulating layer can be disposed between the heat source and the first heat transfer layer. The first transfer layer can comprise a material with isotropic thermal conductivity. The first transfer layer can comprise aluminium, copper, gold, aluminium nitride, brass, iron, a composite material, an elastomer, etc.

According to some embodiments, the system comprises a second heat transfer layer comprising a heat-conducting material configured to transfer the heat from the heat source to the fluid to be heated. The second heat transfer layer can be disposed between the heat source and the insulating layer. The second transfer layer can comprise a material with isotropic thermal conductivity. The second transfer layer can comprise aluminium, copper, gold, aluminium nitride, brass, iron, a composite material, an elastomer, etc.

It should be noted that the system can comprise the first transfer layer, the insulating layer and the second transfer layer. The various layers of the system can be disposed as a stacked layer where each of the layers (which can comprise the heat source) can be in contact and/or securely fixed (by bonding, welding, screwing, or any other fixing means such as clipping, interlocking, etc.). Each of its layers can comprise a surface that substantially extends over the entire surface of the heat source.

According to some embodiments, the electrical power supply comprises an AC-DC converter.

According to some embodiments, the electrical power supply is configured to operate with an external power supply network supplying a voltage ranging between 85 VAC and 260 VAC.

According to some embodiments, the system comprises an applied part fluidly connected to the fluid to be heated and intended to be in contact with the patient.

Preferably, the insulating layer can comprise an insulating material adapted to limit electrical coupling (preferably capacitive coupling) between the heat source and the fluid to be heated, so that the leakage current of the system transferred to the fluid to be heated is less than or equal to 10 µA.

Preferably, the insulating layer can comprise an insulating material adapted to limit capacitive coupling between the heat source and the fluid to be heated, so that the leakage current to ground of the system transferred to the fluid to be heated is less than or equal to 10 µA.

According to some embodiments, the insulating layer comprises a capacitive or inductive magnetic shielding.

A third aspect of the disclosure relates to a system for heating a fluid inducing a patient leakage current (to ground) that is less than 10 µA. The system can comprise a receptacle intended to contain a fluid to be heated, an electrical power supply not connected to ground and powered by an external electrical source, a heating source powered by the electrical power supply configured to heat the fluid present in the receptacle and an interface arranged between the heating source and the receptacle configured to transfer the heat from the heat source to the fluid to be heated.

Preferably, the interface can comprise an insulating layer including an insulating material configured to limit electrical coupling (contactless) (preferably capacitive coupling) between the heating source and the receptacle, so that the heating system cannot induce a patient leakage current that is greater than 10 µA.

The interface (for example, the insulating layer) and the heat source can be disposed as a blanket, where the interface (for example, the insulating layer) can be sandwiched between the heat source and the fluid to be heated. The thickness of the insulating layer can be substantially equal to or less than 10 mm, preferably substantially equal to or less than 8 mm, more preferably substantially equal to or less than 7 mm, for example, ranging between 6.5 and 4 mm (or less).

According to some embodiments, the heat source comprises resistive coils and the insulating layer can be arranged at least above the resistive coils. Preferably, the insulating layer fully covers the heat source.

Preferably, the insulating layer comprises high thermal conductivity, high electrical resistance and/or a low dielectric constant. It can have isotropic thermal conductivity.

According to some embodiments, the specific heat capacity of the insulating layer is substantially equal to or less than 1,400 $J\cdot Kg^{-1}\cdot K^{-1}$, preferably substantially equal to or less than 1,200 $J\cdot Kg^{-1}\cdot K^{-1}$, more preferably substantially equal to or less than 1,100 $J\cdot Kg^{-1}\cdot K^{-1}$.

According to some embodiments, the thermal conductivity of the insulating layer is substantially equal to or greater than 4 $W\cdot m^{-1} K^{-1}$, preferably equal to or greater than 5 $W\cdot m^{-1} K^{-1}$, more preferably equal to or greater than 5 $W\cdot m^{-1} K^{-1}$, for example, ranging between 5 and 6 $W\cdot m^{-1} K^{-1}$.

According to some embodiments, the dielectric constant of the insulating layer is substantially equal to or less than 5, preferably equal to or less than 4, more preferably equal to or less than 3, for example, ranging between 5.5 and 3 (or less).

The insulating layer can comprise a silicon elastomer, boron nitride, a ceramic filled silicon elastomer (which can comprise boron nitride), borosilicate, vitroceramic, aluminium oxide, aluminium nitride, silicon nitride, boron nitride, metal particles, ceramic particles, silicon filled with metal or ceramic particles.

According to some embodiments, the interface further comprises a first heat transfer layer comprising a heat-conducting material configured to transfer the heat from the heat source to the fluid to be heated. The first transfer layer, the insulating layer and the heat source can be disposed as a stacked blanket. The insulating layer can be disposed between the heat source and the first heat transfer layer. The first transfer layer can comprise a material with isotropic thermal conductivity. The first transfer layer can comprise aluminium, copper, gold, aluminium nitride, brass, iron, a composite material, an elastomer, etc.

According to some embodiments, the interface comprises a second heat transfer layer comprising a heat-conducting material configured to transfer the heat from the heat source to the fluid to be heated. The second transfer layer, the insulating layer and the heat source can be disposed as a stacked blanket. The second heat transfer layer can be disposed between the heat source and the first insulating layer. The second transfer layer can comprise a material with isotropic thermal conductivity. The second transfer layer can comprise aluminium, copper, gold, aluminium nitride, brass, iron, a composite material, an elastomer, etc.

Preferably, the interface and the heat source are in contact. In other words, the heat source comprises a surface that is in contact with a surface of the interface. Preferably, there is no space or air gap between these two surfaces.

It should be noted that the interface can comprise the first transfer layer, the insulating layer and the second transfer layer. The various layers of the interface can be disposed as stacked layers (and can comprise the heat source) where each layer can be in contact and/or securely fixed (by bonding, welding, screwing, or other fixing means, such as clipping, interlocking, etc.). Each of its layers can comprise a surface that substantially extends over the entire surface of the heat source. The fixing means can comprise electrically insulating materials, for example, plastic screws.

According to some embodiments, the electrical power supply comprises an AC-DC converter.

According to some embodiments, the electrical power supply is configured to operate with an external power supply network supplying a current ranging between 85 VAC and 260 VAC.

According to some embodiments, the system comprises an applied part fluidly connected to the fluid to be heated and intended to be in contact with the patient.

According to some embodiments, the insulating material is adapted to limit capacitive coupling between the heat source and the fluid to be heated.

According to some embodiments, the electrical power supply is of the class II BF type.

According to some embodiments, the interface comprises a capacitive or inductive magnetic shielding.

According to some embodiments, the receptacle is a container configured to store all the fluid to be heated. According to some embodiments, the receptacle comprises a pocket, through which the fluid to be heated is temporarily received in order to be heated therein. Preferably, this pocket is configured to only receive a volume fraction of the fluid to be heated. According to some embodiments, the volume of fluid increases throughout the treatment. According to some embodiments, the elements moistened by the fluid (to be heated) (for example, the receptacle, the fluid paths, etc.) are disposable elements, whereas some other elements of the system, such as the heating source, the interface, the insulating layer, can be elements that can be reused several times for successive treatments. In this case, the reusable elements are successively used with several disposable elements.

BRIEF DESCRIPTION OF THE DRAWINGS

The invention will be better understood hereafter from some illustrative examples.

Of course, the invention is not limited to these embodiments.

NUMERICAL REFERENCE SIGNS USED IN THE FIGURES

Figure 1:
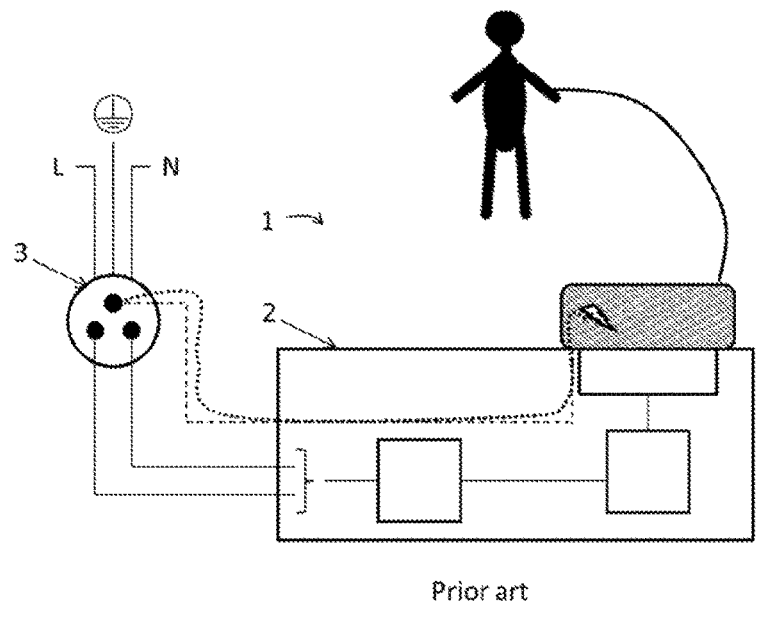
FIG. 1 schematically shows an embodiment of the prior art comprising a power supply connected to ground.

1 System
2 Medical appliance
3 External electrical source or socket
4 Patient
5 Container for fluid to be heated or receptacle for fluid to be heated
6 Heating device or heating source
7 Fluid or electrical connection link
8 Power supply
9 Converter
10 Electrical coupling of the power supply (for example, capacitive coupling)
11 Electrical coupling between the heating source and the fluid to be heated
12 Patient leakage current
13 Fluid line
14 Scales
15 Electronic control device
16 Interface
17 Electrical cable
18 Fluid bag
19 Pump
20 Treatment
21 Loop circuit
22 Heat transfer pipe
101 Heating system
106 Support plate
107 Thermal insulating layer
108 Heat source
109 Insulating layer
110 First heat transfer layer
111 Support for fluid tank
112 Second heat transfer layer
113 Heat transfer means
114 Fixing means
115 Fixing means
118 Screw or cavity for temperature sensor

DETAILED DESCRIPTION OF THE INVENTION

The present document claims the priorities of the following applications: EP19167705.3 filed on 5 Apr. 2019 by Debiotech SA, EP 19167988.5 filed on 8 Apr. 2019 by Debiotech SA and EP19168278.0 filed on 9 Apr. 2019 by Debiotech SA.

In the present document, the detailed description of the invention comprises embodiments of devices, of systems and of methods that are presented by way of an illustration. It is clearly understood that other embodiments can be contemplated and can be added without departing from the scope or the spirit of the invention. Consequently, the following detailed description must not be considered to be limiting.

Unless otherwise stated, the scientific and technical terms that are used in the present document have meanings that are currently used by a person skilled in the art. The definitions provided in this document are mentioned in order to facilitate the understanding of frequently used terms and are not intended to limit the scope of the invention.

The indications of direction used in the description and the claims, such as "top", "bottom", "left", "right", "upper", "lower", and other directions or orientations, are mentioned in order to provide greater clarity with reference to the figures. These indications are not intended to limit the scope of the invention.

The verbs "have", "comprise", "include", or equivalent verbs, are used in the present document in a broad sense and generally mean "include, but not limited thereto".

The term "or" is generally used in a broad sense comprising "and/or", unless the context clearly indicates otherwise.

The expression "central venous catheter" denotes a catheter surgically implanted in a large vein of the thorax or of the neck and comprises a fluid pipe that extends to the superior vena cava. The central venous catheter can be used to administer treatments by the IV route or to take blood for analyses.

The expressions "short peripheral venous catheter" and "long peripheral venous catheter" denote a catheter that is inserted into a vein of the arm or of the hand. Unlike the short peripheral venous catheter, the long peripheral venous catheter comprises a fluid pipe that extends to the superior vena cava. The short peripheral venous catheter comprises a short fluid pipe that extends between 1 and 50 mm in the vein of the patient.

The term "applied part" is generally used to define a part of the device/system/appliance that during normal use comes into contact with the patient in order for the device/system/appliance to fulfil its function. Three types of applied part exist:

CF: the CF type classification is granted for applied parts that will be able to be in direct contact with the heart of the patient (or connected to the heart of the patient). These applied parts must be floating and not connected to ground. This class is the most restrictive and is suitable for direct cardiac applications. The CF type ensures protection against electric shocks to a higher degree than that provided by the BF type;

BF: the BF type classification is granted for applied parts that are in electrical contact with the patient and that must be floating and not connected to ground. For many medical appliances, this classification is therefore stipulated as a minimum by the specific standards. However, it excludes the applied parts that are in direct contact with the heart of the patient. The BF type ensures protection against electric shocks to a higher degree than that provided by the B type;

B: the B type classification is used for applied parts that do not fall within the aforementioned BF and CF categories. Like the BF applied parts, the B classification excludes direct contact with the heart of the patient. The B type applied parts provide the lowest level of protection. They are often passive and connected to ground, without this being compulsory, and do not carry any power or electrical signal to or from the patient.

In the present document, the "leakage current" preferably is a "patient leakage current" measured between the patient connection of the applied part and ground and denotes the current induced by the system flowing from the system to ground via an applied part and/or the patient, for example.

The expression "electrical communication" denotes any intended or unintended transfer of electrical energy from one element to another element or other (for example, a person). This transfer can be direct or indirect, total or partial. For example, when the following is written, "an element electrically connected to a patient", this means that an element and a patient are directly or indirectly connected, so that electrical energy can transition from the element to the patient and/or vice versa. Directly means that there is direct contact between the element and the patient. Indirectly means that there is no direct contact between the element and the patient, in other words the electrical current is transferred by other elements such as water, blood, metals, or other materials or environments allowing electrical energy to be transferred (for example, due to capacitive, inductive coupling or other).

The expression "an electrical power supply not connected to ground" is used in the present document in a broad sense and generally means that either the ground of the external electrical source (socket) is not operational or that it is defective or degraded, or that the electrical power supply is configured so as not to be connected to ground, for example, a class II power supply (appliance having double or reinforced insulation without an accessible metal part. The sockets of class 2 equipment do not have a ground pin).

Preferably, the system comprises a dialysis machine, but the invention is not limited to dialysis machines.

Preferably, the system is configured to carry out a home treatment, for example, a home haemodialysis or peritoneal dialysis treatment.

Preferably, the system is configured to allow the patient to carry out their treatment in various locations and countries without having to verify the status and/or the features of the external electrical power supply (also called external electrical source).

Preferably, the system is adapted to be easily moved by a user (for example, the patient), so as not to hinder the life of the patient. For example, it can involve systems such as those described in the international applications with the following publication numbers: WO 2015/162593, WO 2019/087103, WO 2019/087096. The entire content of these applications is included in this document by way of reference.

The explanations provided hereafter are provided in order to better understand the disclosure, under no circumstances can they be used to limit the scope of the disclosure or the claims.

In this example, the intention is to design a heating system for liquids used in medical treatments such as dialysis. Such a system often forms part of medical machines where, typically, liquids must be brought to a temperature close to that of the human body so as not to cause discomfort, and even complications for the patient. The relevant heating systems are either in-line heating systems, which heat moving liquid, or static heating systems, which heat an amount of stationary liquid in a bag.

Since the power required for heating is high, the machines comprising such a heating system are normally connected to the mains (115 VAC, 230 VAC, etc.). For example, in order to heat a volume of dialysate (greater than or equal to 1 l) with an initial temperature of approximately 15-25° C. in order to reach a temperature of approximately 35-42° C., preferably 37-39° C., the necessary power can be greater than 100 W, preferably ranging between 200 W and 500 W, for example, 400 W. This power level can allow the target temperature to be reached in less than 30 minutes, or less than 20 minutes, or less than 5 minutes. However, as explained above, the connection to the mains requires strict control of the leakage currents that could pass through the patient, during normal operation and in the single fault condition.

Figure 2:
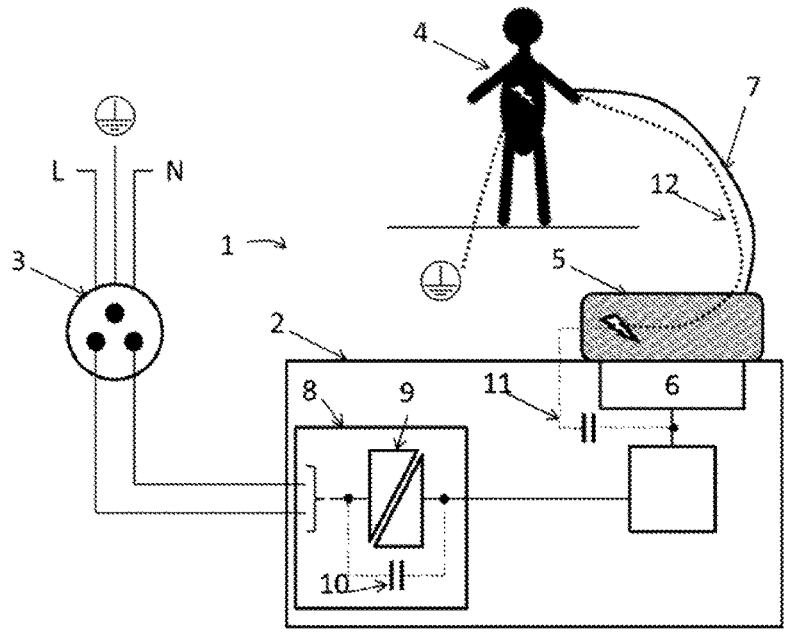
FIG. 2 schematically shows an embodiment where the power supply is not connected to ground.

As disclosed in FIG. 2, in the event of a problem with ground or if the power supply is a class II power supply, the path of the leakage currents passes from the mains cable via the main power supply of the machine, then via the heating system and the fluid line towards the patient themselves, and finally via said patient to ground.

The main power supply generally comprises an AC-DC type converter. Even though the primary side (AC) of this power supply is galvanically insulated from the secondary side (DC), leakage currents from the primary to the secondary can occur since the insulation cannot be perfect. In particular, leakage currents can transfer by electrical coupling (for example, capacitive coupling), which can be due to a parasitic capacitance inside the transformer or to capacitors intentionally inserted between the primary and secondary sides in order to optimize the performance of the power supply in terms of electromagnetic emissions.

For some types of medical appliances, the level of leakage current to ground stipulated by the medical standards is extremely low. Specifically, a "cardiac floating" (CF) type level is stipulated for an appliance with a central venous catheter used for haemodialysis. These standards specify the CF level for applied parts directly in contact with the right atrium of the heart of the patient. A CF level equals 10 µA of current during normal operation and 50 µA of current in a single fault condition. Compared to the "body floating" (BF) level, which is much less restrictive, the leakage current must be ten times less.

Furthermore, reaching the CF level is particularly difficult for class II power supplies (without a connection to ground), which are particularly required when the patients can use the appliance in their home ("home healthcare").

Technically and economically, it is not possible to design a class II AC-DC power supply with a CF leakage current level for the range of powers required in medical heating, which is of the order of a few hundred Watts.

Consequently, the designer must introduce additional insulation in the heating system of the machine in order to reduce the CF level leakage currents to ground. The impact of this electrical insulation with respect to the effectiveness of heat transfer must be taken into account.

The general notion disclosed hereafter is based on the fact that two in-series capacitive couplings reduce the total capacitive coupling. Consequently, the designer can implement a second capacitive coupling in the form of insulation in the heating system, which will be in-series with the capacitive coupling of the AC-DC converter which, for its part, powers the heating system.

Theoretically, the maximum coupling capacitance $C_{CH}$ in the heating system can be expressed as follows:

$$C_{CH} \leq \frac{C_{\frac{AC}{DC}} \cdot C_{CF}}{C_{\frac{AC}{DC}} - C_{CF}},$$

where $C_{AC/DC}$ represents the coupling capacitance in the AC-DC converter itself and $C_{CF}$ represents the theoretical coupling capacitance for obtaining a CF level leakage current. This leakage current can be computed according to the following formula, considering the effective voltage value $U_{RMS}$ and the frequency f of a given electrical network:

$$C_{CF} = \frac{I_{RMS,CF}}{U_{RMS} \cdot 2\pi f}.$$

The effective value of the CF leakage current is assumed to be equal to $I_{RMS,CF}=10$ µA.

The coupling of the AC-DC converter can be estimated based on measurements of the leakage current due to this converter. For a known voltage and frequency of the mains, the following is computed:

$$C_{AC/DC} = \frac{I_{RMS,AC/DC}}{U_{RMS} \cdot 2\pi f}.$$

An example of a computation for a mains voltage of $U_{RMS}$=230V and a network frequency of f=60 Hz shows:

$$C_{CF} = \frac{I_{RMS,CF}}{U_{RMS} \cdot 2\pi f} = 0.115 \text{ nF}.$$

Subsequently, the coupling capacitance in the AC-DC converter is determined. By way of an example, the numbers for converters are provided that allow through between 10 µA (CF level in normal conditions) and 500 µA (BF level in single fault conditions). Knowing $C_{CF}$ and $C_{AC/DC}$, it is then possible to also compute the maximum capacitance that the heating system $C_{CH}$ must have:

| Leakage current passing through the AC-AC converter | | $C_{AC/DC}$ [nF] | $C_{CH}$ [nF] |
| --- | --- | --- | --- |
| 10 µA | CF level 1 converter | 0.115 | ∞ |
| 20 µA | BF level 2 converter | 0.231 | 0.231 |
| 30 µA | BF level 3 converter | 0.346 | 0.173 |
| 50 µA | CF level 4 converter (single fault) | 0.577 | 0.144 |
| 100 µA | BF level 5 converter | 1.153 | 0.128 |
| 500 µA | BF level 6 converter (single fault) | 5.766 | 0.118 |

At the extremes, it can be seen that if the AC-DC power supply already meets the criterion of the CF leakage current to ground, there is no need to be concerned about the coupling capacitance in the heating, which can be unlimited (∞). By contrast, if a BF level AC-DC power supply is selected, the insulation of the heating system must ensure a reduction of the leakage currents in order to reach the CF level.

As previously stated, a class II and CF level AC-DC converter for the desired power range is not realistic. However, converters can be found that are based on a BF model, optimized for weak coupling, which reach a leakage current level between 20 and 100 µA (preferably between 20 and 50 µA, more preferably between 20 and 30 µA), whilst complying with the electromagnetic emission limits. Consequently, additional insulation remains essential. The electrical coupling (including capacitive, inductive and other) in the heating system can be controlled in several ways described in the present document, embodiments can also comprise several possible combinations for reducing the electrical coupling.

Typically, electricity can be converted into heat by metal electro-resistive coils. The surface that these coils expose to the liquid to be heated is a determining factor for coupling, as is the selection of the one or more electrically insulating material(s) interposed between the coils and the liquid. The thickness of these materials and their dielectric features are also important. One of the main problems is to reach a compromise between good electrical insulation and good heat transfer, with both basically being contradictory. This fact is particularly understood when the thickness is considered, since greater thickness ensures better electrical insulation, but at the same time increases the thermal resistance, the weight and the volume of the insulation.

Furthermore, some electrical networks, for example, the American network, have an effective voltage value and a frequency that are lower compared to the examples provided above. In order to obtain a CF level AC-DC power supply for a 115 VAC and 50 Hz network, its coupling capacitance can be higher by a factor of 2.4 compared to the 230 VAC and 60 Hz networks. This makes it easier to produce a CF level medical appliance. A consequence of this observation is that an appliance certified for the European market will also operate on the American market. Conversely, an appliance certified for the American market cannot automatically be considered to be compliant for the European market. With the basis of computation of all the examples provided above being a 230 VAC and 60 Hz electrical network, it is possible to lower the insulation and/or leakage current requirements in the AC-DC power supply if the intention is to only release the appliance on a market where the parameters of the electrical network are more favourable.

Figure 3:
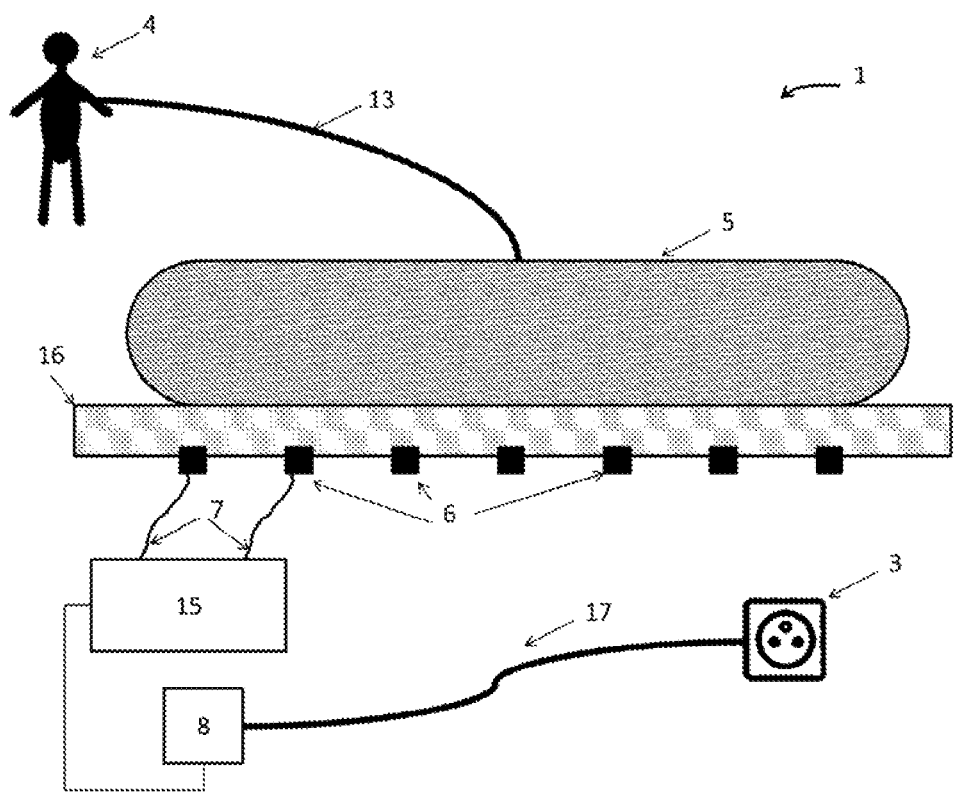
FIG. 3 schematically shows an embodiment according to an aspect of the disclosure.

According to FIG. 3, the system (2) can comprise a receptacle (5) for fluid to be heated (also called medical fluid, for example, a liquid), a fluid line (13) adapted to be in contact with a patient (4) (for example, via an applied part), at least one heating element (6) connected to an electrical power supply (8) via connection cables (17) and/or an electronic management device (15). An interface plate (16) (also called interface) can be interposed between the heating element (6) and the fluid to be heated. All or part of the heating element can be arranged in or against the interface plate (16). The interface plate can be a structure for supporting the heating element (6) or the receptacle (5).

The appliance can comprise an applied part intended to be in contact with a patient and adapted to or configured to be of the CF type. The applied part can comprise a central venous catheter, a long peripheral venous catheter, an element (for example, a fluid pipe) that extends into the superior vena cava, an element implanted/inserted/disposed in a cavity contiguous to the heart of the patient or a part in contact (physical) with the heart of the patient or in contact with the myocardium.

The heating element (6) can comprise resistive coils that convert the electrical energy into heat. The heating element can be disposed parallel to the liquid receptacle (5), as disclosed in FIG. 6.

Preferably, the interface plate (16) can comprise an electrical insulation adapted to avoid any electrical contact with the liquid, so as to protect the patient from excessive leakage currents. The interface plate (16) can comprise one or more layer(s) of the same or of several different material(s), at least one of which is a good electrical insulator. All the layers preferably are good thermal conductors.

The power supply (8) also can be called "medical electrical power supply". The power supply (8) can comprise an AC-AC or AC-DC converter (preferably insulated) connected via an electrical cable (17) to the mains, for example, a socket (3). The socket may or may not comprise a connector connected to ground. The power supply and/or all or part of the appliance (for example, the heating system) is preferably floating and not connected to ground. The converter can separate (insulate) the primary from the secondary, which is equivalent to 2 means of patient protection ("MOPP") from the mains voltage. The power supply can be configured to induce or to induce by design or to induce leakage currents ranging between 500 and 1 µA on the secondary side (preferably less than 100 µA and/or greater than 10 µA). The medical electrical power supply can be installed inside the medical appliance that it powers, mounted on a printed circuit or on the chassis of the medical appliance or arranged in a casing that is external but is electrically connected to the medical appliance.

The receptacle (5) can be configured to receive a liquid bag or can be configured to store a liquid. The receptacle can comprise a heat-conducting and/or electrically insulating material.

The liquid or medical fluid can comprise blood, an ionic liquid, dialysate and/or a pharmaceutical product, etc.

The medical appliance can be configured to carry out a peritoneal dialysis treatment or an extracorporeal blood treatment (for example, haemodialysis).

The fluid path can comprise a blood line configured to circulate blood, a dialysate line configured to circulate dialysate and/or a filter. The fluid path can also comprise a valve configured to open or close all or part of the fluid path, a catheter, a tank, etc.

The medical appliance can also comprise one or more pump(s) configured to move the liquid in the fluid line and one or more temperature sensor(s) that can be arranged on the fluid line and/or against or in the interface plate (16). The electronic management device can be coupled to the heating element, to the pump and/or to the sensor, and/or can be configured so as to manage the heating and/or the movement of the liquid.

All or part of these elements (for example: the power supply, the electronic device, the heating element, etc.) can be arranged inside a casing of the medical appliance.

Even if, for the sake of simplification, the figures most often disclose a heating system that is similar to a means for heating a bag, the various embodiments described in this document can use various heating means that are described thereafter.

Figure 4A:
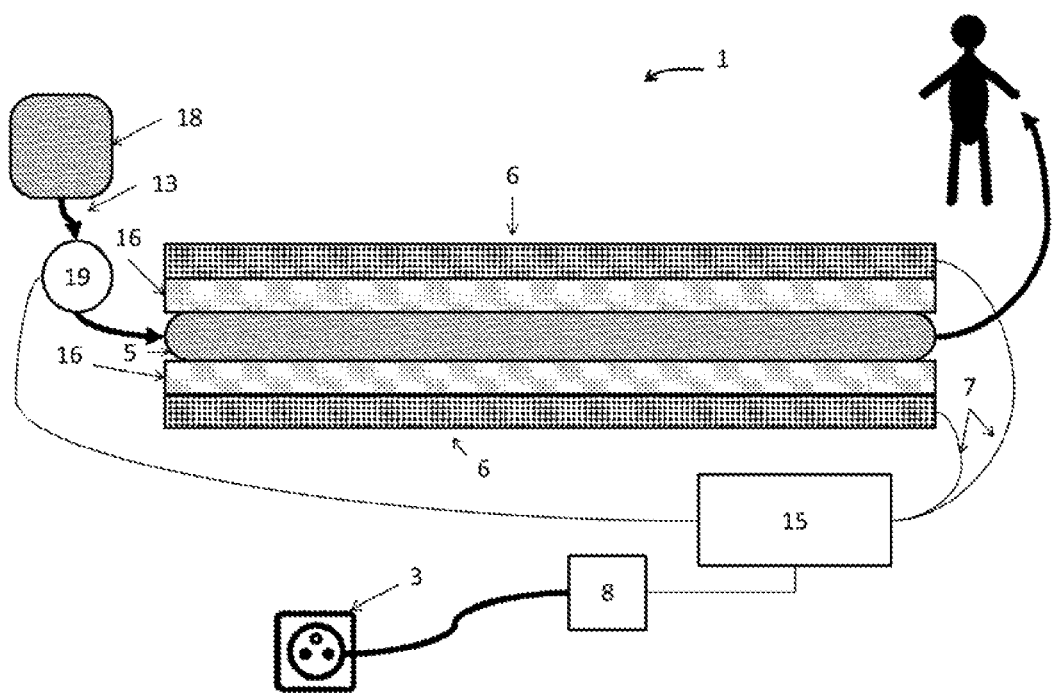
FIG. 4a schematically shows an embodiment with in-line heating.

In-line heating involves heating a fluid that passes through a fluid path (for example, a pocket). FIG. 4a discloses a heating system (1) comprising an electrical power supply (8) connected to a control device (15) adapted to control and/or power the heating source (6) and optionally a pump (19). The system further comprises a fluid bag (18) fluidly connected to the receptacle (5) of fluid to be heated. The fluid is moved using the pump (19) and, while the fluid passes through the receptacle (5), it is heated by the heat source (6). The interface (16) and the heat source are configured to limit electrical coupling, as disclosed in the document. The embodiment disclosed by FIG. 4a shows two facing heat sources and the interfaces and the receptacle are disposed between these two heat sources. An alternative embodiment could comprise a single heat source. In these embodiments, the fluid enters at a temperature T1 and must leave at a given temperature T2. The heat source therefore must add enough energy to reach this given temperature T2 throughout the treatment. Temperature sensors upstream and/or downstream of the receptacle allow the device to control and/or adjust the heating power.

Figure 4B:
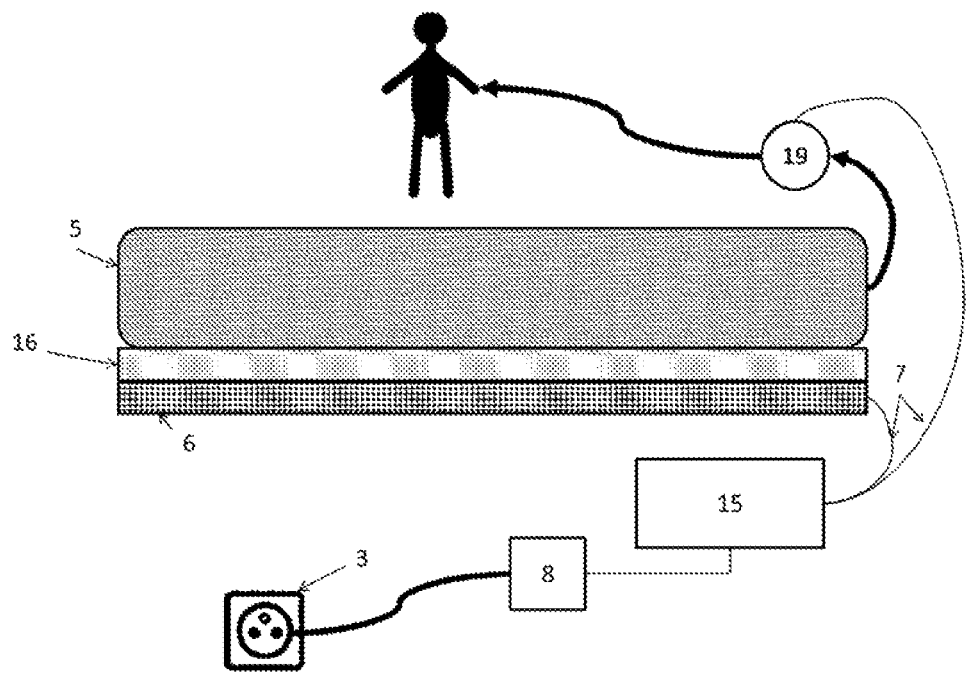
FIG. 4b schematically shows an embodiment with bag heating.

Heating a bag involves heating a fluid that is entirely stored in a bag. FIG. 4b discloses a heating system (1) comprising an electrical power supply (8) connected to a control device (15) adapted to control and/or to power the heating source (6) and optionally a pump (19). In this embodiment, the receptacle is a container (for example, a bag), in which the fluid to be heated is stored. Typically, all the fluid to be heated is stored in the receptacle and at the start of treatment its entire content must be heated to the desired temperature, then the control device maintains this temperature.

Figure 4C:
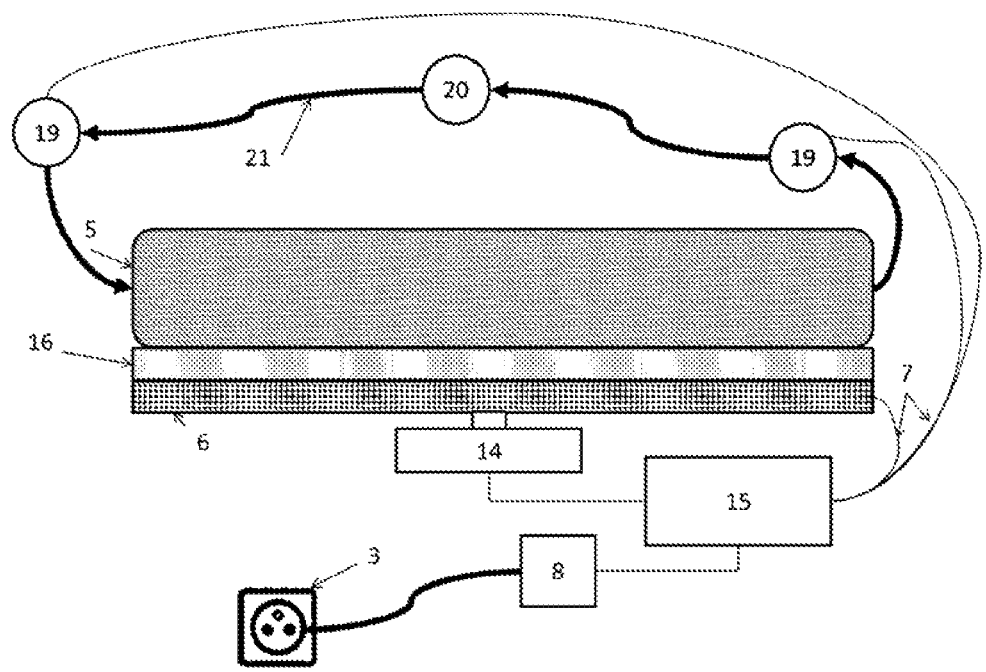
FIG. 4c schematically shows an embodiment with a loop circuit.

FIG. 4c discloses a system for heating a receptacle (5) with a loop fluid circuit (21). In the context of a dialysis system, it can involve a dialysate circuit that comprises a sorbent. In this case, the circuit can comprise a dialysate source (which can be the receptacle (5)), one or more pumps (19), a dialysis machine and/or a sorbent. FIG. 4c schematically shows the treatment using reference sign (20). It can involve the dialysis machine, the sorbent or other element(s) required for the treatment. This reference sign (20) can be located before or after a pump, between two pumps, etc. In this embodiment, the patient is not shown, but they can be electrically connected (as for the other embodiments) via the dialysate circuit that is heated, via the dialysis machine and via the blood circuit. In this embodiment, during the treatment the volume of fluid in the loop circuit (21) can increase, since as the treatment will be carried out, the treatment will remove ultrafiltrate from the patient (including water), which will be added to the initial volume of dialysate (which may have been initially stored in the receptacle or in a separate container). The purpose of the sorbent is to "purify" the ultrafiltrate by removing some components from this ultrafiltrate, such as urea, etc. The sorbent can also remove components that are necessary for the treatment, thus the system can further comprise a device for adding other components (additives) and mixing them, for example, in the receptacle. Thus, in some embodiments, the heating system will initially heat an initial volume of fluid (for example, 1-2 L of initial dialysate), then will maintain a volume of fluid at a temperature, which will increase throughout the treatment (up to 4-8 L, for example).

More specifically, the heating systems disclosed in FIGS. 4b and 4c require heating a greater initial volume (greater than or equal to 1 l or at least greater than 500 ml or 750 ml) than that of FIG. 4a. The heating system (FIGS. 4b and 4c) can be configured to heat this initial volume (for example, initially to 15-25° C.) in order to reach a target temperature of 33-42° C., preferably between 37 and 39° C. in a short time (less than or equal to 30 minutes, preferably less than or equal to 20 minutes, for example, 5 minutes for 1 l of dialysate with a heating power of 400 W), so that the patient can rapidly begin their treatment. This then requires having a powerful enough heat source, for example, greater than 100 W, more preferably greater than 200 W or 300 W (for example, 400 W). Ideally, the interface must comprise a material evenly diffusing the heat over all (or nearly all) the surface of the interface (material with isotropic thermal conductivity), and preferably with a high heat transfer coefficient. In this document, the proposed solutions also allow CF level (less than 10 µA) leakage currents (to ground) to be achieved.

In some embodiments, the heating system comprises a weighing device (14) intended to determine the amount of fluid contained in the receptacle (5).

In some embodiments, the system can comprise one or more temperature sensor(s) intended to instruct the control device in order to control the system, including the heat source.

In some embodiments, one or more control device(s) can comprise one or more processor(s) connected to the heat source, to the sensor(s) and/or to the pump(s). This/these control device(s) can be configured to control and/or monitor the one or more heat source(s), the sensor(s) and/or the pump(s).

Solutions Contemplated for Limiting Electrical Coupling

Several solutions have been contemplated in order to improve the electrical insulation between the heating system and the fluid path. The improvement vectors can be:

assuming that the coupling is mainly inductive (magnetic) ($\Phi = \iint \mu \cdot H(r) \cdot dA$):

an insulating material with low magnetic permeability ($\mu \downarrow$) or a magnetic shielding;

an increase in the distance between the heat source and the fluid path ($r \uparrow, H \downarrow$;

a reduction in the magnetic surface that the heat source exposes to the fluid path ($A \downarrow$;

assuming that the coupling is mainly capacitive ($C = \varepsilon \cdot A / d$):

an insulating material with low permittivity ($\varepsilon \downarrow$, dielectric constant);

an increase in the distance between the heat source and the fluid path ($d \uparrow$);

a reduction in the capacitive surface that the heat source exposes to the fluid path ($A \downarrow$).

Magnetic Shielding

Some embodiments can comprise an interface comprising a magnetic shielding between the heating plate and the liquid. This shielding can be made up of one or more sheet(s) of a material with high magnetic permeability µ. The material can be ferromagnetic, it can comprise nickel-iron alloys, the crystalline structure of which may have been modified by an annealing process in a protected atmosphere (hydrogen). Such a material could increase the permeability compared to other iron-based materials by a factor of approximately 40. The one or more shielding sheet(s) can be preformed before an annealing process, for example, by buffering.

The shielding can comprise one or more 0.01 to 1 mm thick metal sheet(s), preferably each between 0.1 and 0.5 mm. The total thickness, the weight and the bulk of the shielding thus can be low. The transfer of heat through the shielding layer may not be severely affected.

The shielding can be configured so as to divert the magnetic field generated by the residual AC currents in the resistive coils (and not to cancel all or part of the magnetic field). The force lines may no longer pass through the liquid, but through the shielding, the leakage currents thus can be significantly reduced. With shielding with high magnetic permeability, this phenomenon can operate at very low frequencies, such as the frequencies of the electrical network (for example, 50/60 Hz).

The magnetic shielding can be arranged in the interface plate (6) and/or on one or more wall(s) of the receptacle.

The heating system can comprise resistive coils that exist in combination with the magnetic shielding.

The heating system becomes much less dependent on the choice of power supply, it optionally can settle for a BF type power supply without compromising the level of CF leakage currents required for the medical device as a whole (in particular for the applied part).

A heating plate system with resistive coils can be supported. In order to control the temperature in a closed loop (via the electronic management device), temperature sensors can be placed in the interface plate.

Increasing the Distance Between the Heat Source and the Fluid Path

Irrespective of the type of coupling, the heat source can be spaced apart from the fluid path without compromising heat transfer. According to an aspect of the invention, heat transfer can occur by convection, not (or not only) by conduction.

According to some embodiments, the heating system comprises a heat transfer device that can contain a heat transfer fluid. Such a system can comprise a material that stores heat well (high specific heat, for example, the heat transfer fluid) without transferring it by conduction (low thermal conductivity) and that can be electrically insulating (in addition, for example, to a low dielectric constant).

The conventional fluids (liquids, for example) used for cooling applications (heat engine, etc.) are water (with or without additives) and oils. For a heating application in a medical appliance, the temperature range is similar (<100° C.), and the same liquids can be suitable. Water must be treated (purified) in order to become a poor electrical conductor.

TABLE 1

List of different liquids/fluids that can function as a heat carrier.

| | | Relative permittivity (dielectric constant) [—] at 25° C. and 1 MHz | Thermal conductivity [W/mK] at 25° C. | Specific heat [J/kgK] at 25° C. |
|---|---|---|---|---|
| Water | Fluid | 80 | 0.6 | 4180 |
| Ethylene Glycol | Fluid | 37 | 0.25 | 2210 |
| Mineral oil | Fluid | 2.0-2.2 | 0.15 | 1670 |
| Liquid paraffin | Fluid | 2.2 | 0.1-0.3 | 2130 |
| Silicone oil | Fluid | 2.2-2.8 | 0.1 | 1670 |

Figure 5:
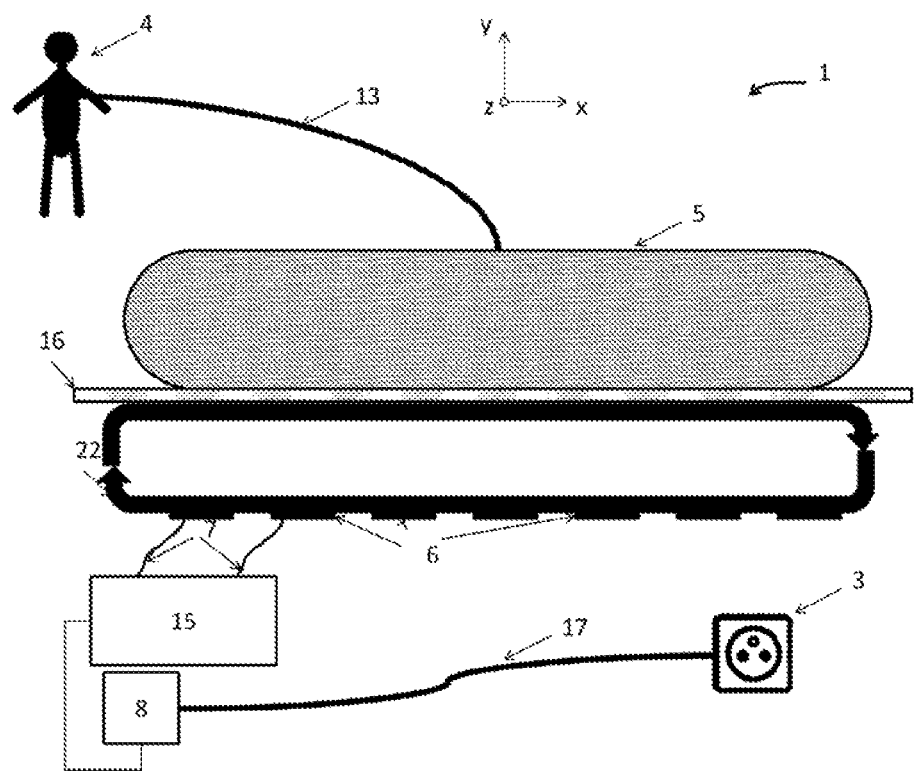
FIG. 5 schematically shows an embodiment according to an aspect of the disclosure.

An example of separating the heat source from the medical fluid that is based on transferring heat by convection is schematically shown in FIG. 5. According to this embodiment, the heating system comprises a heat transfer device (22), which allows the heat to be transferred from the heating elements, whilst spacing apart the receptacle from the heating element.

Heat is firstly transferred from the heat source (heating element) to the heat transfer device. In the event that the heat transfer device comprises a heat transfer fluid, this fluid can circulate inside the heat transfer device (in one or more closed circuit(s)), the geometry and the arrangement of which are adapted to the application. It can be moved by free convection, or by forced convection (for example, via a pump that can be managed by the electronic management device). Secondly, the heat transfer device transfers the heat to the liquid in the receptacle by conduction. The transfer can be direct or through the interface plate, which can comprise an additional layer of heat-conducting material (for example).

The heat transfer fluid can be or can comprise water, oil, an additive and/or a liquid with a liquid/vapour phase change as a function of the considered temperatures.

The heat transfer device can comprise walls. These walls can internally define a fluid path, in which the heat transfer fluid moves (as disclosed above). In order to benefit from good electrical insulation between the heat source and the medical fluid, the heat transfer device (for example, the walls) can comprise an electrically insulating material (plastic, ceramic, etc.). The parts of the heat transfer device (for example, the walls) that are not used for convection or conduction of heat to or from the heat transfer fluid can comprise a thermal insulation in order to improve the yield of the heat transfer and to avoid unwanted heating of the inside of the medical appliance.

The operating principle of this solution can require a fluid with high specific heat; in this case, the heating inertia due to the fluid volume cannot be neglected. Therefore, it is worthwhile optimizing the geometry of the system in order to reduce the fluid volume to a minimum.

The heating system becomes much less dependent on the choice of power supply, it optionally can settle for a BF type power supply without compromising the level of CF leakage currents required for the medical device as a whole (in particular for the applied part).

A heating plate system with resistive coils can be supported. In order to control the temperature in a closed loop (via the electronic management device), temperature sensors can be placed in the interface plate.

Low Permittivity Insulating Interface

The solution involving increasing the distance between the heat source and the fluid path can be problematic since at the same time it adds thermal resistance and compromises the correct transfer of heat. Furthermore, thicker insulation can increase the weight of the appliance, as well as the thermal inertia, which is problematic for temperature control. Reducing the electrical surface (magnetically or capacitively active) of the heating system may not be desirable, since, for the same transferred power, the temperatures would increase locally.

By assuming in this case that the capacitive coupling is dominant, a third option exists for reducing the coupling, namely that of finding an insulating material with low permittivity E (reference: $\varepsilon_{vacuum}=1$, $\varepsilon_{air}=1.4$). At the same time, this material must have good thermal conductivity and low specific heat. This latter parameter characterizes its thermal inertia.

Thus, according to some embodiments, the heating system comprises an interface comprising an insulating layer with low dielectric permittivity.

Table 2 below shows a list of potential materials. After analyzing various options, some ceramics, such as boron nitride (formula: BN) can be interesting due to their high thermal conductivity (much better than that of plastics), low permittivity (similar to plastics), and, finally, lower specific heat compared to plastics. Other ceramics, in particular from the glass family, or natural rock plates, are less adapted to the application of a conduction heating system, since they exhibit very low thermal conductivity around 1-4 W/mk.

According to some embodiments, the interface can comprise one or more part(s) of ceramic combined with other (layers of) material(s).

According to some embodiments, the interface can comprise an insulating layer comprising a silicon matrix filled with metal or ceramic particles. The ceramic (or metal) particles allow good thermal conductivity, whereas the silicon allows good electrical insulation and has a low dielectric constant. Thus, the silicons filled with metal or ceramic particles can be a good compromise between the good thermal and electrical properties of the ceramics, as well as the economic factor, since the pure technical ceramics can be more expensive to manufacture.

The heating system becomes much less dependent on the choice of power supply, it optionally can settle for a BF type power supply without compromising the level of CF leakage currents required for the medical device as a whole (in particular for the applied part).

A heating plate system with resistive coils can be supported. In order to implement temperature control in a closed loop (via the electronic management device), temperature sensors can be placed in the interface plate.

TABLE 2

List of different materials that can function as electrical insulators and thermal conductors.

| | | Relative permittivity (dielectric constant) [—] @ 25° C. and 1 MHz | Thermal conductivity [W/mK] @ 25° C. | Specific heat [J/kgK] @ 25° C. |
|---|---|---|---|---|
| Celanese Coolpoly ® D3612 (Polyamide 6, PA6) | Plastic | 3.6 | 1.2 | 1200 |
| Celanese Coolpoly ® D5506 (Liquid Crystal Polymer, LCP) | Plastic | 3.8 | 1.9 | ? |
| Pyrex glass (borosilicate) | Ceramic | 4.3-5 | 1 | 750 |
| Macor ® | Ceramic | 6 | 1.5 | 800 |
| Vitroceram | Ceramic | 6-7 | 1.7 | 800-850 |
| Aluminium oxide ($Al_2O_3$) | Ceramic | 8-11 | 12-40 | 450-950 |
| Aluminium nitride (AlN) | Ceramic | 7-9 | 60-210 | 780-820 |
| Silicon nitride ($Si_3N_4$) | Ceramic | 7-8 | 17-100 | 350-700 |
| Boron nitride (BN) | Ceramic | 3-5 | 12-130 | 640-860 |
| Euro Technologies EU-TPL200 | Silicon filled ceramic | 3.2 | 6 | ? |
| Marble | Natural rock | 8 | 2-3 | 880 |
| Granite | Natural rock | 7-9 | 1.7-4 | 790 |

After having determined the one or more material(s) selected for this insulating layer (for example, for the purpose of limiting capacitive coupling), the thickness of said layer must be defined. If the modelling of the coupling is simplified to a single layer of insulating material with a thickness $d_{ISO}$ and a surface $A_{ISO}$, the relation between coupling capacitance and thickness is expressed with the ideal capacitor formula:

$$d_{ISO} = \varepsilon_0 \cdot \kappa \cdot \frac{A_{ISO}}{C_{CH}}.$$

The permittivity of the vacuum $\varepsilon_0$ is a universal physical constant, whereas the relative permittivity (dielectric constant) K only depends on the selected insulating material.

In order to simplify the disclosure, the present document provides, by way of an example, a silicon matrix containing ceramic particles such as boron nitride, but other materials (in particular those listed in this document) can allow the same aim to be achieved with dimensioning that is likely to be different.

TABLE 3

List of possible materials of the particle filled silicon matrix type.

| Designation | Thermal conductivity | Volume resistivity | Dielectric constant | Density |
|---|---|---|---|---|
| Euro Technologies EU-TPL200 Thickness 5 mm, 200° C. max, UL 94 HB | 6 W/mK | $5.0 \times 10^{13}$ Ωcm | 3.2 | 1.4 g/cm³ |
| Ziitek TIF ™ 600G Series Thickness 5 mm, 160° C. max, UL 94 V0 | 6.2 W/mK | $5.2 \times 10^{13}$ Ωcm | 5.5 | 2.95 g/cm³ |
| Ziitek TIF ™ 800 Series Thickness 5 mm, 160° C. max, UL 94 V0 | 5.0 W/mK | $5.0 \times 10^{13}$ Ωcm | 5.5 | 2.69 g/cm³ |
| Laird Tflex ™ HD700 Thickness 5 mm, 200° C. max, UL 94 V0 | 5.0 W/mK | $1.4 \times 10^{14}$ Ωcm | 5.0 | 3.3 g/cm³ |
| Laird Tpli ™ 200 Thickness 5 mm, 200° C. max, UL 94 HB | 6.0 W/mK | $5 \times 10^{13}$ Ωcm | 3.4 | 1.4 g/cm³ |

In the example used herein, the insulating layer comprises a silicon matrix containing ceramic particles. This insulating layer can be in the form of a flexible blanket. This material has a high and isotropic heat transfer coefficient, around 5-6.2 W/mK in the best cases, as well as low relative permittivity of approximately κ=3. This type of material thus can be of interest for application in a heating system. The common application of these materials actually involves transferring heat from a hot body, such as an electronic component, to a radiator.

Using the table listing the coupling capacitances $C_{CH}$ that are required as a function of the coupling by the capacitance $C_{AC/DC}$ in the power supply, the following thicknesses are obtained for=3 and $A_{ISO}$=20×20 cm$^2$:

| $C_{AC/DC}$ [nF] | $C_{CH}$ [nF] | $d_{iso}$ [mm] min required |
|---|---|---|
| 0.115 | ∞ | 0 |
| 0.231 | 0.231 | 4.6 |
| 0.346 | 0.173 | 6.14 |
| 0.577 | 0.144 | 7.37 |
| 1.153 | 0.128 | 8.29 |
| 5.766 | 0.118 | 9.02 |

For realistic AC-DC power supplies with a leakage current between 20 and 30 µA, an approximately 5 to 7 mm thick insulating layer (of the boron nitride filled silicon type) needs to be interposed. To avoid hindering the heat transfer, the insulating material must be a good thermal conductor.

Figure 6:
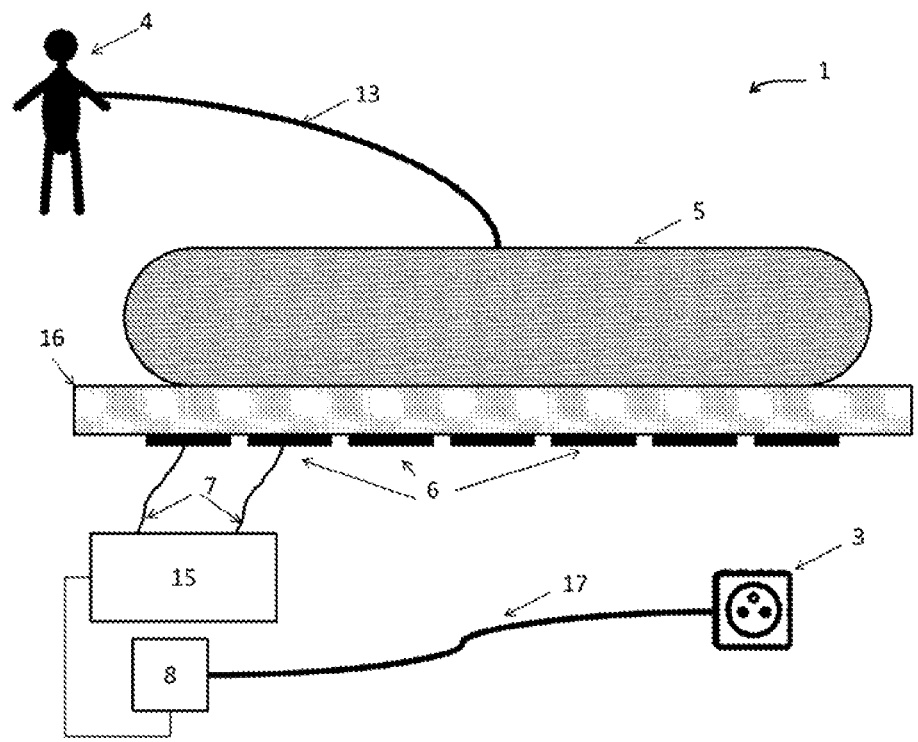
FIG. 6 schematically shows an embodiment according to an aspect of the disclosure with horizontal strips.

Reduction of the Capacitive Surface that the Heat Source Exposes to the Fluid Path FIG. 6 schematically shows a heating system where the heat source (6) comprises "conventional" coils. These conventional coils are strips, the width of which is arranged parallel to the interface plate in order to increase the heating surface. This parallel arrangement can be the source of the strong capacitive coupling, and therefore of the transfer of leakage currents. In fact, the coils occupy a significant share of the surface available in the heating plate. The advantage of this assembly is that transferring heat by conduction through the plastic, but electrically insulating, heat-conducting layer is very direct and effective.

Figure 7:
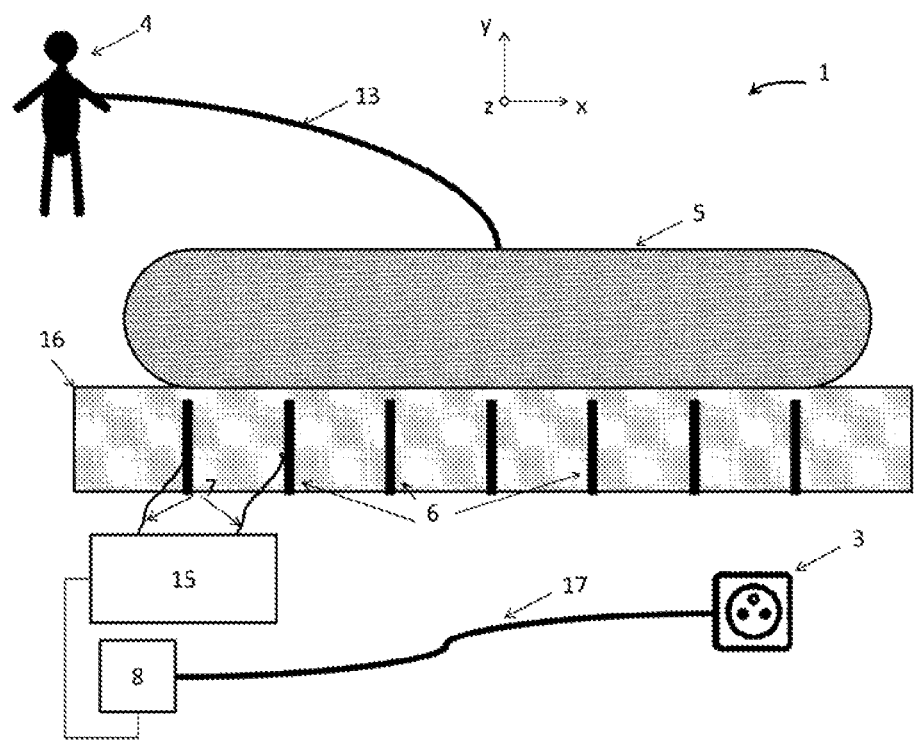
FIG. 7 schematically shows an embodiment according to an aspect of the disclosure with vertical strips.

In order to optimize the metal surface that the coils/strips expose to the dialysate, one of the contemplated solutions is to place the width of the strips perpendicular to the receptacle (5) (for example, in a vertical position of the strips as opposed to the horizontal position of the strips of FIG. 6) as shown in FIG. 7. For example, the width of the strips can define a perpendicular plane (Y; Z) relative to the plane (X; Z) defined by the interface plate (16) and/or the receptacle (5). Thus, the exposed metal surface is significantly reduced, it can basically depend on the thickness of the coils and not on their width. However, heat transfer by the layer (for example, the interface plate) is less direct.

This position (vertical position of the coils) will only expose the thickness of the heating element, and not its width, to the liquid. In the case whereby the flat heating wires have a thickness-to-width ratio that exceeds 1:10 (one to ten), the metal surface exposed to the dialysate will be reduced by a factor of 10 (ten) at least. This would have a direct effect on the capacitive coupling and thus on the leakage currents.

The heating system becomes much less dependent on the choice of power supply, it optionally can settle for a BF type power supply without compromising the level of CF leakage currents required for the medical device as a whole (in particular for the applied part).

A heating plate system with resistive coils can be supported. In order to control the temperature in a closed loop (via the electronic management device), temperature sensors can be placed in the interface plate.

Even though the heat transfer to the dialysate is less direct than in the conventional solution, new plastic and composite materials (for example, plastics filled with metal or ceramic particles) currently allow very good thermal conduction, whilst being electrical insulators at the same time. The desired thinness of the insulating material will enable work with a lower temperature gradient. This is equivalent to a lower requirement in terms of insulation between the heat source and the rest of the machine. Furthermore, the bulk of a solution with heat transfer by conduction is less compared to a solution with transfer by radiation or by convection, or any other solution that aims to reduce the level of the leakage currents by separating the heat source from the dialysate.

The heat plate system outlined in FIG. 7 can comprise a plastic part (which can be the interface plate) with the grooves for the heating coils. With respect to the plastic part, it is important to select a material that is thermally conductive (thermal conductivity k>1 W/mK), but electrically insulating. The grooves for the resistive coils must be a few tens of millimetres wide, whereas the depth will be a few millimetres. The plastic part can be manufactured via an injection process or any other manufacturing process that is known to a person skilled in the art.

Example of an Embodiment

Figure 8:
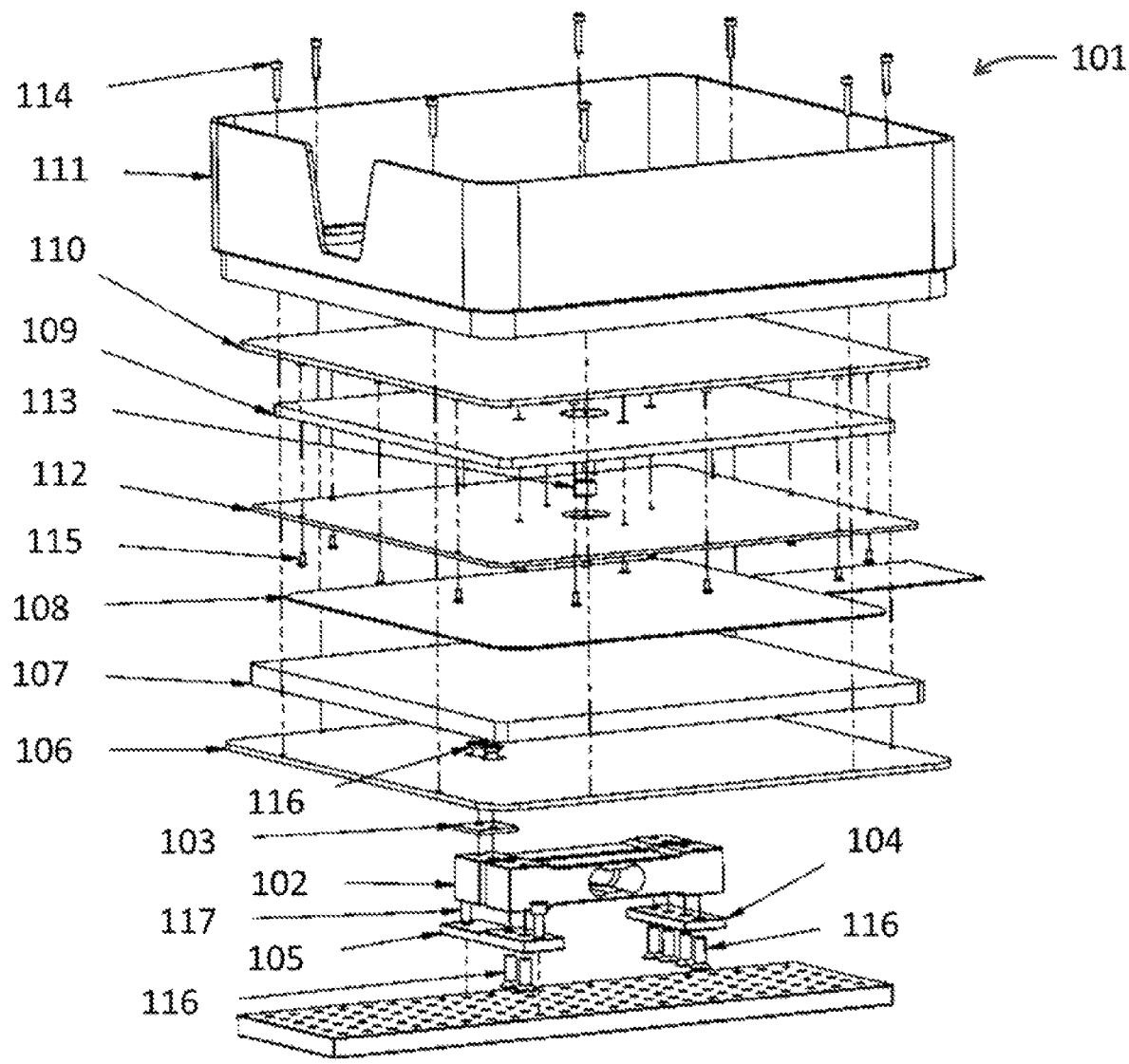
FIG. 8 discloses an exploded view of an embodiment with a weighing system.

According to some embodiments, as disclosed in FIG. 8, the heating system (101) comprises a heat source (108) and an interface comprising an insulating layer (109) configured to limit the electrical coupling (in particular capacitive coupling) between the heat source (108) and the fluid to be heated (not shown herein), in order to limit the leakage current of the system to less than 10 µA.

Preferably, the system comprises one or more stacked layer(s). Furthermore, the interface can comprise at least one of the following additional layers:
 a first heat transfer layer (110); and/or
 a second heat transfer layer (112).

The first heat transfer layer (110) can be configured to come into contact with the receptacle of fluid to be heated (not shown herein). This first heat transfer layer (110) can comprise an upper surface and a lower surface. The upper surface can be intended to be in contact with the receptacle of fluid to be heated. The lower surface can be intended to be in contact with the insulating layer (for example, an upper surface of the insulating layer). The heat transfer layer can extend over all or part of the insulating layer (preferably almost all). The first transfer layer can comprise aluminium, copper, gold, aluminium nitride, brass, iron, a composite material, an elastomer, etc. The first heat transfer layer (112) can be configured to substantially evenly diffuse the heat received at the receptacle.

The second heat transfer layer (112) can be configured to come into contact with the heat source (108). This second heat transfer layer (112) can comprise an upper surface and a lower surface. The upper surface can be intended to be in contact with the insulating layer (109). The lower surface can be intended to be in contact with the heat source. The second heat transfer layer can extend over all or part of the insulating layer and/or of the heat source (preferably over almost all of at least one of the two). The second transfer layer can comprise aluminium, copper, gold, aluminium nitride, brass, iron, a composite material, an elastomer, etc. The second heat transfer layer (112) can be configured to substantially evenly diffuse the heat originating from the heat source to the insulating layer.

According to some embodiments, the interface is configured so that there is no empty space or air gap between the various layers of the interface. To this end, the interface can comprise fixing means (devices) (115) allowing these layers to be secured together. These layers can be assembled/fixed together by screwing, bonding, welding, stamping, binding, etc. Preferably, these fixing means are configured so as not to promote electrical coupling and they can be produced from electrically insulating materials, for example, made of plastic (plastic screw, etc.).

The system can further comprise a reception tank configured to receive the receptacle of fluid to be heated. This reception tank can comprise rigid walls (111). The first heat transfer layer (110) can form the bottom of this reception tank. In this case, the interface (at least the first heat transfer layer (110)) is securely fixed to the rigid walls (111) in order to form the reception tank.

The receptacle of fluid to be heated (not shown herein) can be a pocket, a bag, a container comprising a compartment, inside which the fluid to be heated is heated. The receptacle can comprise a flexible wall made, for example, from a plastic material or other derivative. The receptacle can comprise a surface (for example, a lower surface) intended to be in contact with a surface of the interface (for example, an upper surface).

According to some embodiments, the heating system comprises a thermally insulating layer (107) configured to avoid heat dissipation to unwanted locations and to prevent the heat source from heating inside the system, which would involve a loss of energy and could cause premature ageing of the other elements of the system such as the power supply, the converter, the control device, etc.

According to some embodiments, a support plate (106) allows all the various assembled elements/layers (in particular the interface and the heat source) to be supported without a space or an air gap between (these elements or layers) via, for example, fixing means (114) that can be means like those described above. The support plate is configured to provide the assembly with a certain amount of mechanical resistance, which with the receptacle can weigh between 2 and 8 kg.

According to some embodiments, the heating system further comprises a weighing means (102) fixed to the assembly (heat source and interface), for example, to the support plate (106).

Figure 9:
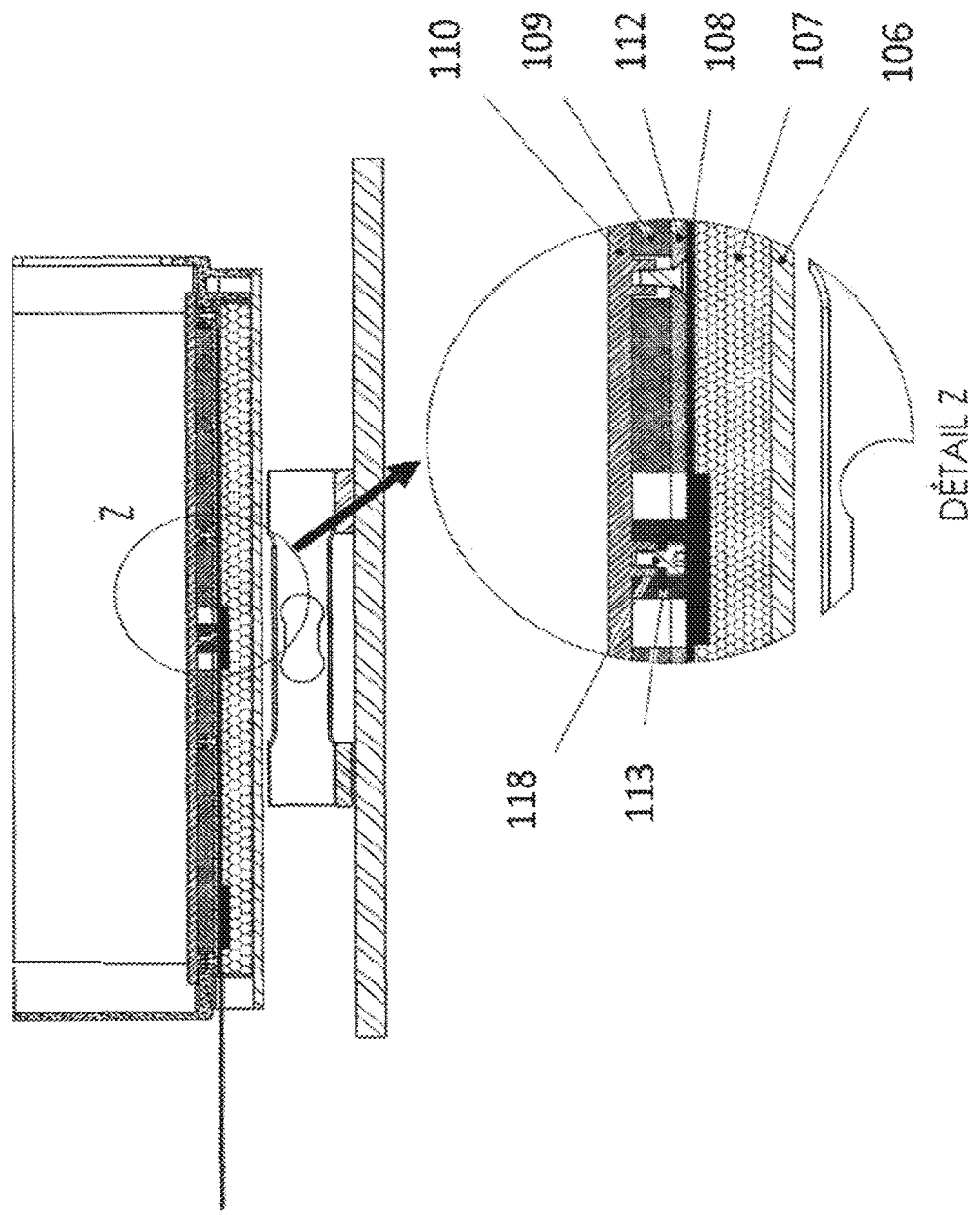
FIG. 9 discloses an embodiment with a weighing system and an exploded view.

FIG. 9 discloses the assembly and the detail Z. According to some embodiments, the system can comprise a temperature sensor. This temperature sensor can be arranged in the cavity (118) or in the heat source (108). In this latter case, a heat transfer means (113) can be arranged between the transfer layer (110) and the temperature sensor, so that the temperature of the receptacle is transmitted to the temperature sensor. Depending on the requirements (dimensional constraint or depending on the arrangement of the elements), the layers of the interface can comprise openings, preferably at locations where there are no resistive coils of the heat source, in order to avoid any electrical coupling.

Combination(s)

According to some embodiments, the heating system comprises one or more of the aforementioned solution(s).

The heating system can be powered by a BF type power supply and comprise at least one of the aforementioned solutions. The power supply can be configured to induce or induces leakage currents ranging between 100 and 1 µA, preferably between 70 and 10 µA, more preferably between 50 and 10 µA, and even more preferably between 30 and 10 µA, whereas the heating system in its entirety can thus induce a leakage current that is less than or equal to 10 µA.

Simple combination examples are provided in this case. Other combinations are possible that are based on all or part of the solutions described in this document.

Example of a Conventional Construction 1

A medical appliance comprising:
a class II BF type power supply with a leakage current of approximately 70 µA comprising an insulated AC-DC converter;
a heating element, the coil/strips of which are disposed conventionally (horizontally) (as in FIG. 2 or 6).
The leakage current measured at the applied part is 17 µA.

Example of a Conventional Construction 2

A medical appliance comprising:
a class II BF type power supply with a leakage current of approximately 35 µA comprising an insulated AC-DC converter;
a heating element, the coil/strips of which are disposed conventionally (horizontally) (as in FIG. 2 or 6).
The leakage current measured at the applied part is 14 µA.

Example of a Conventional Construction 3

A medical appliance comprising:
a class II BF type power supply with a leakage current of approximately 70 µA comprising an insulated AC-AC converter;
a heating element, the coil/strips of which are disposed conventionally (horizontally) (as in FIG. 2 or 6).
The leakage current measured at the applied part is 25 µA.

Example of a First Combination

A medical appliance comprising:
a class II BF type power supply with a leakage current of approximately 70 µA comprising an insulated AC-DC converter;
a heating element, the coil/strips of which are disposed conventionally (horizontally) (as in FIG. 2 or 6);
an interface plate comprising a composite material such as a silicon matrix filled with ceramic particles (or other material with similar insulating features, as disclosed in the present document).
The leakage current measured at the applied part is less than 10 µA.

Example of a Second Combination

A medical appliance comprising:
a class II BF type power supply with a leakage current of approximately 70 µA comprising an insulated AC-DC converter;
a heating element, the coil/strips of which are disposed vertically (as in FIG. 7).
The leakage current measured at the applied part is less than 10 µA.

Example of a Third Combination

A medical appliance comprising:
a class II BF type power supply with a leakage current of approximately 70 µA comprising an insulated AC-DC converter;
a heating element, the coil/strips of which are disposed vertically (as in FIG. 7);
an interface plate comprising a composite material such as a silicon matrix filled with ceramic particles (or other material with similar insulating features, as disclosed in the present document).
The leakage current measured at the applied part is less than 10 µA.

Example of a Fourth Combination

A medical appliance comprising:
a class II BF type power supply with a leakage current of approximately 30 µA comprising an insulated AC-DC converter;
a heating element, the coil/strips of which are conventionally disposed (horizontally) (as in FIG. 2 or 6);
an interface plate comprising a composite material such as a silicon matrix filled with ceramic particles (or other material with similar insulating features, as disclosed in the present document).
The leakage current measured at the applied part is less than 10 µA.

Example of a Fifth Combination

A medical appliance comprising:
a class II BF type power supply with a leakage current of approximately 30 µA comprising an insulated AC-DC converter;
a heating element, the coil/strips of which are disposed vertically (as in FIG. 7).
The leakage current measured at the applied part is less than 10 µA.

Example of a Sixth Combination

A medical appliance comprising:
a class II BF type power supply with a leakage current of approximately 30 µA comprising an insulated AC-DC converter;
a heating element, the coil/strips of which are disposed vertically (as in FIG. 7);
an interface plate comprising a composite material such as a silicon matrix filled with ceramic particles (or other material with similar insulating features, as disclosed in the present document).
The leakage current measured at the applied part is less than 10 µA.

Example of a Seventh Combination

A medical appliance comprising:
a class II BF type power supply with a leakage current of approximately 70 µA comprising an insulated AC-AC converter;
a heating element, the coil/strips of which are disposed conventionally (horizontally) (as in FIG. 2 or 6);
an interface plate comprising a shielding as disclosed in this document.
The leakage current measured at the applied part is less than 10 µA.

Example of an Eight Combination

A medical appliance comprising:
a class II BF type power supply with a leakage current of approximately 70 µA comprising an insulated AC-AC converter;
a heating element, the coil/strips of which are disposed conventionally (horizontally) (as in FIG. 2 or 6);
an interface plate comprising a shielding configured to limit capacitive coupling, as disclosed in this document.
The leakage current measured at the applied part is less than 10 µA.

Example of a Ninth Combination

A medical appliance comprising:
a class II BF type power supply having a leakage current of approximately 70 µA comprising an insulated AC-AC converter;
a heating element, the coil/strips of which are disposed vertically (as in FIG. 7);
an interface plate comprising a shielding configured to limit electrical coupling (for example, capacitive coupling), as disclosed in this document.
The leakage current measured at the applied part is less than 10 µA.

The invention claimed is:

1. A system for heating a fluid, the system causing a patient leakage current that is less than 10 µA, the system comprising:
a receptacle configured to hold a fluid to be heated;
an electrical power supply not connected to ground and powered by an external electrical source;
a heating source powered by the electrical power supply configured to heat the fluid present in the receptacle; and
an interface disposed between the heating source and the receptacle, the interface being configured to transfer heat from the heating source to the fluid to be heated, the interface including an insulating layer having an insulating material configured to limit an electrical coupling between the heating source and the receptacle, so that the system for heating a fluid does not cause a patient leakage current that is greater than 10 µA, the insulating material comprising a silicon matrix containing metal particles or ceramic particles.

2. The system according to claim 1, wherein the insulating layer and the heating source are arranged as a stacked blanket, and
wherein the insulating layer is sandwiched between the heating source and the fluid to be heated.

3. The system according to claim 1, wherein the insulating layer comprises a ceramic filled silicon elastomer comprising boron nitride, borosilicate, vitroceramic, aluminum oxide, aluminum nitride, or silicon nitride.

4. The system according to claim 1, wherein the interface further comprises a first heat transfer layer having a heat-conducting material configured to transfer the heat from the heating source to the fluid to be heated.

5. The system according to claim 4, wherein the interface further comprises a second heat transfer layer comprising a heat-conducting material configured to transfer the heat from the heating source to the fluid to be heated.

6. The system according to claim 1, wherein the electrical power supply is configured to not to be connected to ground.

7. The system according to claim 1, wherein the electrical power supply is configured to operate with an external electrical source supplying a voltage ranging between 85 VAC and 260 VAC.

8. The system according to claim 1, further comprising:
a patient body application part electrically connected to the patient.

9. The system according to claim 8, wherein the patient body application part is in contact with a heart, a myocardium, or a cavity contiguous to the heart of a patient.

10. The system according to claim 1, wherein the insulating material is configured to limit a capacitive coupling between the heating source and the fluid to be heated.

11. The system according to claim 1, wherein the electrical power supply is a class II power supply.

12. The system according to claim 1, wherein the heating source includes heating strips.

13. The system according to claim 1, wherein the electrical power supply includes an insulated AC-AC or AC-DC converter.

14. A dialysis treatment system comprising:
the heating system according to claim 1.

15. The dialysis treatment system according to claim 14, wherein the fluid to be heated is blood or dialysate.

16. The dialysis treatment system according to claim 14, further comprising:
a patient body application part electrically connected to the patient,
wherein the patient body application part comprises a central venous catheter or a long peripheral venous catheter.

* * * * *